United States Patent [19]
Ciotti et al.

[11] Patent Number: 5,011,681
[45] Date of Patent: Apr. 30, 1991

[54] FACIAL CLEANSING COMPOSITIONS

[75] Inventors: Susan L. Ciotti, Derby; Eric G. Spengler, Cheshire; George E. Deckner, Trumbull, all of Conn.

[73] Assignee: Richardson-Vicks, Inc., Shelton, Conn.

[21] Appl. No.: 419,895

[22] Filed: Oct. 11, 1989

[51] Int. Cl.$^5$ ................................................ A61K 7/02
[52] U.S. Cl. ........................................ 424/81; 424/83; 424/68
[58] Field of Search ...................... 424/83, 68, 81, 401; 514/938, 846; 252/174.23, DIG. 5

[56] References Cited

U.S. PATENT DOCUMENTS

| | | | |
|---|---|---|---|
| 3,406,238 | 10/1968 | Freyermuth | 424/81 |
| 3,475,369 | 10/1969 | Blunt | 424/69 |
| 3,915,921 | 10/1975 | Schlatzer, Jr. | 260/17.4 |
| 4,029,682 | 6/1977 | Foulks | 260/410.7 |
| 4,049,792 | 9/1977 | Flsnau | 424/66 |
| 4,120,948 | 10/1978 | Shelton | 424/66 |
| 4,252,826 | 2/1981 | Boelle et al. | 424/361 |
| 4,327,751 | 4/1982 | Evans | 424/62 |
| 4,390,442 | 6/1983 | Quick | 252/106 |
| 4,509,949 | 4/1985 | Huang et al. | 586/558 |
| 4,597,963 | 7/1986 | Deckner | 424/59 |
| 4,663,157 | 5/1987 | Brock | 424/59 |
| 4,699,780 | 10/1987 | Jennings | 424/64 |
| 4,781,914 | 11/1988 | Deckner | 424/59 |
| 4,810,489 | 3/1989 | Murray et al. | 424/59 |
| 4,822,603 | 5/1989 | Farris | 424/DIG. 5 |
| 4,885,159 | 12/1989 | Miyake | 424/81 |
| 4,919,934 | 4/1990 | Deckner | 424/401 |

FOREIGN PATENT DOCUMENTS 255157  6/1987  European Pat. Off. .

OTHER PUBLICATIONS

Soap/Cosmetics/Specialities, "Hydrophobically Modified, 'Carbopol' Resins", May 1987.
BF Goodrich Technical Publication Number CP3.
BF Goodrich Technical Publication Number PC-31.
Cosmetics & Toiletries, "A New Waterproofing Agent for Sunscreen Products", vol. 102, No. 3, p. 107, Mar. 1987.
Cosmetics and Toiletries, "Novel Cosmetic Emulsions", vol. 101, No. 11, p. 125, Nov. 1986.

Primary Examiner—Thurman K. Page
Assistant Examiner—Demetra J. Mills
Attorney, Agent, or Firm—David K. Dabbiere; Douglas C. Mohl; Jack D. Schaeffer

[57] ABSTRACT

Disclosed are facial cleansing compositions in the form of an oil-in-water emulsion which contain specific surfactants with an HLB above about 10 in combination with specific polyalphaolefins and specific carboxylic copolymers which provide improved cleansing efficacy as well as improved rinsability and improved skin feel (such as a nongreasy feeling).

10 Claims, No Drawings

FACIAL CLEANSING COMPOSITIONS

TECHNICAL FIELD

This invention relates to improved facial cleansing compositions for removal of make-up and the like in the form of an oil-in-water emulsion.

BACKGROUND OF THE INVENTION

Cosmetic cleansing compositions for removing make-up and the like are in wide use today and are marketed in a variety of forms such as creams, lotions, astringents, etc. Such cleansing compositions are useful in facial and body cleansing, especially to remove make-up, oil, dirt, soil and other undesirable materials on a person's face or body.

There are two "traditional" cleansing creams. The first, cold creams, are based on the beeswax/borax formulation. The second are semi-translucent liquefying formulations using a mixture of hydrocarbon oils and waxes.

Cold cream formulations are centuries old. The earliest preparations were primarily animal and vegetable fats and oils; typically beeswax and olive oil. Water was later added to the molten beeswax and olive oil. This resulted in a "cooling" effect during use through the evaporation of the water on the skin. These first products were unstable and subject to rancidity. In time, sweet almond oil replaced the heavier olive oil, borax was introduced as a stabilizer, and then spermaceti (whale oil) was added to soften the product. Later modifications included changing from almond oil to mineral oil, with rose water and rose oil added for fragrance purposes.

More modern cleansing creams incorporate other fatty acid esters for emulsification rather than borax and substitute fatty acids and fatty alcohols for beeswax. Current cleansers contain, for example, synthetic emulsifiers instead of borax, as well as the traditional beeswax/borax systems.

After use of many skin cleansing compositions, such as cold creams, the user will typically follow such application with a bar soap in order to remove any remaining residue left behind as well as to obtain a "clean feel".

It has been found that the facial cleansing compositions of the present invention in the form of an oil-in-water emulsion which contain specific surfactants with an HLB above about 10 in combination with specific polyalphaolefins and specific carboxylic copolymers provides improved cleansing efficacy as well as improved rinsability and improved skin feel (such as non-greasy feeling). It is therefore an object of the present invention to provide an improved facial cleansing composition which thoroughly cleanses the skin by removing, for example, dirt and oil as well as difficult to remove make-up, waterproof mascara and the like.

It is a further object of the present invention to provide an improved facial cleansing composition which has superior rinsing.

It is still a further object of the present invention to provide an improved facial cleansing composition with improved skin feel after rinsing.

These and other objects will become readily apparent from the detailed description that follows.

SUMMARY OF THE INVENTION

The present invention relates to cleansing compositions for removing make-up and the like in the form of an oil-in-water emulsion comprising:

a. from about 0.5% to about 10% of a surfactant with an HLB greater than about 10 selected from the group consisting of anionic, nonionic, zwitterionic, amphoteric and ampholytic surfactants and mixtures thereof;

b. from about 2% to 30% of polyalphaolefin of the formula:

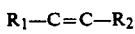

wherein $R_1$ and $R_2$ are independently from about $C_{20}$ to about $C_{30}$ alkyl, wherein said polyalphaolefin has a viscosity of from about 2 to about 4 centistokes at 100° C.; and c. from about 0.025% to about 0.75% of a carboxylic copolymer comprising polymers of a monomeric mixture containing 95.9 to 98.8 weight percent of an olefinically unsaturated carboxylic monomer selected from the group consisting of acrylic, methacrylic and ethacrylic acids, about 1 to about 3.5 weight percent of an acrylate ester of the formula:

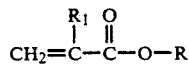

wherein R is an alkyl radical containing 10 to 30 carbon atoms and $R_1$ is hydrogen, methyl or ethyl, and 0.1 to 0.6 weight percent of a polymerizable cross-linking polyalkenyl polyether of a polyhydric alcohol containing more than one alkenyl ether group per molecule wherein the parent polyhydric alcohol contains at least 3 carbon atoms and at least 3 hydroxyl groups.

All percentages and ratios used herein are by weight of the total composition and all measurements made at 25° C., unless otherwise designated.

DETAILED DESCRIPTION OF THE INVENTION

Surfactant

The surfactant component of the compositions of the present invention are selected from anionic, nonionic, zwitterionic, amphoteric and ampholytic surfactants, as well as mixtures of these surfactants. Such surfactants are well-known to those skilled in the detergency art. The surfactants useful in the present invention have an HLB of greater than about 10 and preferably from about 10 to about 14 and more preferably from about 11 to about 14 and most preferably from about 12 to about 14.

The HLB (short for "Hydrophile-Lipophile Balance") value system is fully described, and values for various materials are provided, in the publication *The HLB System. A Time-Saving Guide to Emulsifier Selection* (published by ICI Americas Inc., Wilmington, Dela.; 1984), the disclosures of which are incorporated herein by reference in their entirety.

The most common type of anionic surfactants can be broadly described as the water-soluble salts, particularly the alkali metal salts, of organic sulfuric reaction products having in the molecular structure an alkyl radical containing from about 8 to about 22 carbon atoms and a radical selected from the group consisting of sulfonic acid and sulfuric acid ester radicals. Important examples of these surfactants are sodium, ammonium or potassium alkyl sulfates, especially those obtained by sulfating the higher alcohols produced by reducing the glycerides of tallow or coconut oil; sodium or potassium alkyl benzene sulfonates in which the alkyl group contains from about 9 to about 15 carbon atoms, especially those of the types described in U.S. Pat. Nos. 2,220,099 and 2,477,383, incorporated herein by reference; sodium alkyl glyceryl ether sulfonates, especially those ethers of the higher alcohols derived from tallow and coconut oil; sodium coconut oil fatty acid monoglyceride sulfates and sulfonates; sodium or potassium salts of sulfuric acid esters of the reaction product of one mole of a higher fatty alcohol (e.g., tallow or coconut oil alcohols) and about three moles of ethylene oxide; sodium or potassium salts of alkyl phenol ethylene oxide ether sulfates with about three to about twenty moles of ethylene oxide; sodium or potassium salts of alkyl phenol ethylene oxide; sodium or potassium salts of alkyl phenol ethylene oxide ether sulfates with about four units to about twenty units of ethylene oxide per molecule and in which the alkyl radicals contain about 9 carbon atoms; the reaction product of fatty acids esterified with isethionic acid and neutralized with sodium hydroxide where, for example, the fatty acids are derived from coconut oil; sodium or potassium salts of fatty acid amide of a methyl taurine in which the fatty acids, for example, are derived from coconut oil; and others known in the art, such as those specifically set forth in U.S. Pat. Nos. 2,486,921, 2,486,922 and 2,396,278, incorporated herein by reference.

An important type of useful anionic surfactants are soaps. Soaps which can be used as the surfactant in the present compositions include alkali metal (e.g. sodium or potassium) soaps of fatty acids containing from abut 8 to about 24, preferably from about 10 to about 20, carbon atoms. The fatty acids used in making the soaps can be obtained from natural sources such as, for instance, plant or animal-derived glycerides (e.g., palm oil, coconut oil, babassu oil, soybean oil, castor oil, tallow, whale oil, fish oil, grease, lard, and mixtures thereof). The fatty acids can also be synthetically prepared (e.g. by oxidation of petroleum stocks or by the Fischer-Tropsch process). Also useful are alphamethyl sulfoesters (available as Alpha-Step® from Stepan Chemical).

Alkali metal soaps can be made by direct saponification of the fats and oils or by the neutralization of the free fatty acids which are prepared in a separate manufacturing process. Particularly useful are the sodium and potassium salts of the mixtures of fatty acids derived from coconut oil and tallow, i.e., sodium and potassium tallow and coconut soaps.

The term "tallow" as used herein in connection with fatty acid mixtures refers to acids which typically have an approximate carbon chain length distribution of 2.5% $C_{14}$, 29% $C_{16}$, 23% $C_{18}$, 2% pamitoleic, 41.5% oleic and 3% linoleic acid (the first three fatty acids listed are saturated). Other mixtures with similar distributions, such as the fatty acids derived from various animal tallows and lard, are also included within the term tallow. The tallow can also be hardened (i.e., hydrogenated) to convert part or all of the unsaturated fatty acid moieties to saturated fatty acid moieties.

The term "coconut oil" as used herein refers to fatty acid mixtures which typically have an approximate carbon chain length distribution of about 8% $C_8$, 7% $C_{10}$, 48% $C_{12}$, 17% $C_{14}$, 9% $C_{16}$, 2% $C_{18}$, 4oleic, and 2% linoleic acid (the first six fatty acids listed being saturated). Other sources having similar carbon chain length distribution, such as palm kernel oil and babassu oil, are included with the term coconut oil.

Nonionic surfactants may be broadly defined as compounds produced by the condensation of alkylene oxide groups (hydrophilic in nature) with an organic hydrophobic compound, which may be aliphatic or alkyl aromatic in nature. The length of the hydrophilic or polyoxyalkylene radical which is condensed with any particular hydrophobic group can be readily adjusted to yield a water-soluble compound having the desired degree of balance between hydrophilic and hydrophobic elements.

For example, a well-known class of nonionic surfactants is commercially available under the trade name "Pluronic" marketed by the BASF Wyandotte Corporation. These compounds are formed by condensing ethylene oxide with a hydrophobic base formed by the condensation of propylene oxide with propylene glycol. The hydrophobic portion of the molecule which, of course, exhibits water-insolubility has a molecular weight of from about 1500 to about 1800. The addition of polyoxyethylene radicals to this hydrophobic portion tends to increase the water-solubility of the molecule as a whole and the liquid character of the products is retained up to the point where polyoxyethylene content is about 50% of the total weight of the condensation product.

Other suitable nonionic surfactants include, for example:

(i) The polyethylene oxide condensates of alkyl phenols, e.g., the condensation products of alkyl phenols having an alkyl group containing from about 6 to about 12 carbon atoms in either a straight chain or branched chain configuration, with ethylene oxide, the said ethylene oxide being present in amounts equal to from about 5 to about 25 moles of ethylene oxide per mole of alkyl phenol The alkyl substituent in such compounds may be derived from polymerized propylene, diisobutylene, octane, and nonane, for example. Examples of compounds of this type include nonyl phenol condensed with about 12 moles of ethylene oxide per mole of phenol; dinonyl phenol condensed with about 15 moles of ethylene oxide per mole of phenol; and diisooctyl phenol condensed with about 15 moles of ethylene oxide per mole of phenol. Commercially available nonionic surfactants of this type include Igepal® CO-630, marketed by the GAF Corporation,; and Triton X-45, X-114, X-100, and X-102, all marketed by the Rohm & Haas Company.

(ii) Those derived from the condensation of ethylene oxide with the product resulting from the reaction of propylene oxide and ethylene diamine-products which may be varied in composition depending upon the balance between the hydrophobic and hydrophilic elements which is desired. Examples are compounds containing from about 40% to about 80% polyoxyethylene by weight and having a molecular weight of from about 5,000 to about 11,000 resulting from the reaction of ethylene oxide groups with a hydrophobic base constituted of the reaction product of ethylene diamine and excess propylene oxide, said base having a molecular weight of the order of 2500 to 3000. Examples of this type of nonionic surfactant include certain of the commercially available Tetronic ® compounds, marketed by Wyandotte Chemical Corporation.

(iii) The condensation product of aliphatic alcohols having from 8 to 36 carbon atoms, in either straight or branched chain configuration, with ethylene oxide, e.g., a coconut alcohol ethylene oxide condensate having from 7 to 40 moles of ethylene oxide per mole of coconut alcohol. Examples of commercially available nonionic surfactants of this type include Tergitol ® 15-S-9 (the condensation product of $C_{11}$–$C_{15}$ secondary alcohol with 9 moles ethylene oxide), marketed by Union Carbide Corporation; Neodol ® 45-9 (the condensation product of $C_{14}$–$C_{15}$ liner alcohol with 9 moles of ethylene oxide), Neodol 45-7 (the condensation product of $C_{14}$–$C_{15}$ liner alcohol with 7 moles of ethylene oxide), Neodol ® 45-4 (the condensation product of $C_{14}$–$C_{15}$ linear alcohol with 4 moles of ethylene oxide), marketed by Shell Chemical Company, and Kyro ® EOB (the condensation product of $C_{13}$–$C_{15}$ linear alcohol with 9 moles of ethylene oxide), marketed by The Procter & Gamble Company.

(iv) Trialkyl amine oxides and trialkyl phosphine oxides wherein one alkyl group ranges from 10 to 18 carbon atoms and two alkyl groups range from 1 to 3 carbon atoms; the alkyl groups can contain hydroxy substituents. Specific examples include dodecyl (di-2-hydroxyethyl)amine oxide and tetradecyl dimethyl phosphine oxide.

Zwitterionic surfactants comprise the betaine and betaine-like compounds wherein the molecule contains both basic and acidic groups which form an inner salt giving the molecule both cationic and anionic hydrophilic groups over a broad range of pH values.

Some common examples of these surfactants are described in U.S. Pat. Nos. 2,082,275, 2,702,279 and 2,555,082, incorporated herein by reference. Suitable zwitterionic surfactants have the formula

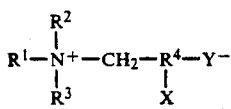

wherein $R^1$ is an alkyl radical containing from about 8 to about 22 carbon atoms, $R^2$ and $R^3$ contain from about 1 to about 3 carbon atoms, $R^4$ is an alkylene chain containing from about 1 to about 4 carbon atoms, X is selected from the group consisting of hydrogen and a hydroxyl radical, Y is selected from the group consisting of carboxyl and sulfonyl radicals and wherein the sum of the $R^1$, $R^2$, and $R^3$ radicals is from about 14 to about 26 carbon atoms.

Other useful nonionic surfactants include $C_{12}$ to $C_{36}$ ethoxylated fatty acids $C_{12}$ to $C_{36}$ mono- and diglycerides, $C_{12}$ to $C_{36}$ mono- and disorbitan esters, $C_{12}$ to $C_{36}$ propylene glycol or ethylene esters each having from about 4 to about 20 moles of ethylene oxide per molecule; $C_8$ to $C_{36}$ polyglyceryl monoesters having repeating glycerin units of between about 8 and 20; $C_8$ to $C_{36}$ alkylpolyglucosides having between about 1 and 10 repeating glycose units; $C_8$ to $C_{14}$ sucrose monoesters; $C_{12}$ to $C_{36}$ carboxylated ethoxylated fatty alcohols having between about 1 and 20 moles of ethylene oxide per molecule.

Amphoteric and ampholytic surfactants which can be either cationic or anionic depending upon the pH of the system are represented by detergents such as dodecyl-beta-alanine, N-allkyltaurines such as the one prepared by reacting dodceylamine with sodium isethionate according to the teaching of U.S Pat. No. 2,658,072, N-higher alkylaspartic acids such as those produced according to the teaching of U.S. Pat. No. 2,438,091, and the products sold under the trade name "Miranol" and described in U S. Pat. No. 2,528,378, said patents being incorporated herein by reference.

Preferred for use herein are anionic surfactants, nonionic surfactants and mixtures thereof.

Additional surfactants useful in the present invention can be found in McCutcheon's *Deterqents and Emulsifiers*, North American Ed. pages 317-324 (1986), incorporated herein by reference.

The surfactant component is present at a level of from about 0.5% to about 10%, preferably from about 0.5% to about 5% and most preferably from about 0.5% to about 2%.

Polyalphaolefins. The compositions of the present invention also essentially comprise one or more of a polyalphaolefin of the formula:

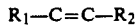

wherein $R_1$ and $R_2$ are independently from about $C_{20}$ to about $C_{30}$ alkyl.

Useful polyalphaolefins have an average molecular weight of from about 250 to about 350 daltons, and a viscosity of from about 2 to about 4 centistokes at 100° C. The viscosity can be measured by means of a glass capillary viscometer as set forth in ASTM method D-88.

The polyalphaolefins are available, for example, from the Emery Chemical Specialties Group as E-3002.

The polyalphaolefins typically comprise from about 2% to about 30%, preferably from about 5% to about 15% and most preferably from about 8% to about 11% of the total composition.

Carboxylic Copolymer

The carboxylic copolymers useful in the present invention are polymers of a monomeric mixture containing 95.9 to 98.8 weight percent of an olefinically unsaturated carboxylic monomer selected from the group consisting of acrylic, methacrylic and ethacrylic acids, about 1 to about 3.5 weight percent of an acrylate ester of the formula:

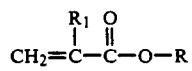

wherein R is an alkyl radical containing 10 to 30 carbon atoms and $R_1$ is hydrogen, methyl or ethyl, and 0.1 to 0.6 weight percent of a polymerizable cross-linking polyalkenyl polyether of a polyhydric alcohol containing more than one alkenyl ether group per molecule wherein the parent polyhydric alcohol contains at least 3 carbon atoms and at least 3 hydroxyl groups.

Preferably, these polymers contain from about 96 to about 97.9 weight percent of acrylic acid and from about 2.5 to about 3.5 weight percent of acrylic esters wherein the alkyl group contains 12 to 22 carbon atoms, and $R_1$ is methyl, most preferably the acrylate ester is stearyl methacrylate. Preferably, the amount of cross-linking monomer is from about 0.2 to 0.4 weight percent. The preferred crosslinking monomers are allyl pentaerythritol, trimethylolpropane diallylether or allyl sucrose. These polymers are fully described in U.S. Pat. No. 4,509,949, Huang et al., issued Apr. 5, 1985.

The carboxylic monomers useful in the production of polymers used in this invention are the olefinically-unsaturated carboxylic acids containing at least one activated carbon-to-carbon olefinic double bond, and at least one carboxyl group.

The preferred carboxylic monomers are the acrylic acids having the general structure

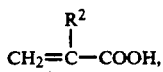

wherein $R^1$ is a substituent selected from the class consisting of hydrogen, halogen, and the cyanogen ($-C\equiv N$) groups, monovalent alkyl radicals, monovalent alkaryl radicals and monovalent cycloaliphatic radicals. Of this class, acrylic, methacrylic, and ethacrylic acid are most preferred. Another useful carboxylic monomer is maleic anhydride or the acid. The amount of acid used will be from about 95.5 to about 98.9 weight percent of the total monomers used. More preferably the range will be from about 96 to about 97.9 weight percent.

The polymers are crosslinked with a polyfunctional vinylidene monomer containing at least 2 terminal $CH_2<$ groups, including for example, butadiene, isoprene, divinyl benzene, divinyl naphthlene, allyl acrylates, and the like. Particularly useful crosslinking monomers for use in preparing the copolymers are polyalkenyl polyethers having more than one alkenyl ether grouping per molecule. The most useful possess alkenyl groups in which an olefinic double bond is present attached to a terminal methylene grouping, $CH_2=C<$. Most preferred is Carbomer 1342 (available as Carbopol® 1342 from B.F. Goodrich).

These polymers comprise from about 0.025 to about 0.75, preferably from about 0.05 to about 0.25 and most preferably from about 0.075 to about 0.175.

Optional Components

Emulsifier. Emulsifiers are preferably included in the compositions of the present invention, preferably comprising from about 0.05% to about 10% by weight of the composition, and most preferably from about 2% to about 8%. Preferred emulsifiers are anionic or monionic although other types may also be used. Most preferred is anionic. Suitable emulsifiers are disclosed in, for example, U.S. Pat. No. 3,755,560, issued Aug. 28, 1973, to Dickert et al.; U.S. Pat. No. 4,421,769, issued Dec. 20, 1983, to Dixon et al.; and McCutcheon's *Detergents and Emulsifiers*, North American Edition, 1983; with the disclosures of these references being incorporated herein by reference.

Other types of emulsifiers useful in the compositions of the present invention include ethoxylated fatty acids, ethoxylated fatty alcohol esters, ethoxylated alcohol, phosphated esters, polyoxyethylene fatty ether phosphates, fatty acid esters, fatty acid amides, acyl lactylates, soaps and mixtures thereof. Fatty alcohols such as cetyl and stearly alcohol, and cetearyl alcohol are also regarded as emulsifiers for purposes of the present invention. Examples of such emulsifiers include polyoxyethylene (8) stearate, myristyl ethoxy (3) myristate, polyoxyethylene (100) monostearate, lauric diethanolamide, stearic monoethanolamide, sodium steroyl-2-lactylate.

Emollients. The compositions of the present invention also preferably comprise at least one emollient. Preferred emollients are volatile silicone oils, non-volatile emmolients, and mixtures thereof. The compositions of the present invention more preferably comprise at least on volatile silicone oil which functions as a liquid emollient, or especially in a mixture of volatile silicone oils and non-volatile emollients, The term "volatile", as used herein, refers to those materials which have a measurable vapor pressure at ambient temperature.

Volatile silicone oils useful in the compositions of the present invention are preferably cyclic or linear polydimethylsiloxanes containing from about 3 to about 9, preferably from about 4 to about 5, silicon atoms. The following formula illustrates cyclic volatile polydimethylsiloxanes useful in the compositions disclosed herein:

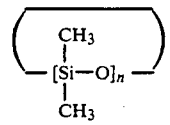

wherein n equals about 3 to about 7. Linear polydimethylsiloxanes contain from about 3 to about 9 silicon atoms per molecule and have the following general formula:

$$(CH_3)_3Si-O-[Si(CH_3)_2-O]_nSi(CH_3)_3$$

wherein n equals about 1 to about 7. Linear volatile silicone materials generally have viscosities of about 0.5 centistokes at 25° C. while cyclic materials typically have viscosities of less than about 10 centistokes. A description of various volatile silicone oils is found in Todd, et al., "Volatile Silicone Fluids for Cosmetics", *Cosmetics & Toiletries, 91*, pages 27–32 (1976), the disclosures of which are incorporated by reference herein in their entirety.

Examples of preferred volatile silicone oils useful herein include: Dow Corning 344, Dow Corning 345, and Dow Corning 200 (manufactured by Dow Corning Corp.); Silicone 7207 and Silicone 7158 (manufactured by the Union Carbide Corp.); SF 1202 (manufactured by General Electric); and SWS-03314 (manufactured by SWS Silicones, Inc.).

The present compositions also preferably contain one or more non-volatile emollients. Such materials include fatty acid and fatty alcohol esters, hydrocarbons, non-volatile silicone oils, and mixtures thereof. Emollients among those useful herein are described in 1 *Cosmetics, Science and Technology* 27–104 (M. Balsam and E. Sagarin, Ed.; 1972), and U.S. Pat. No. 4,202,879, to Shelton, issued May 13, 1980 (both incorporated by reference herein).

Non-volatile silicone oils useful as an emollient material include polyalkylsiloxanes, polyalklyarylsiloxanes, and polyethersiloxane copolymers. The essentially non-volatile polyalkyl siloxanes useful herein include, for example, polydimethyl siloxanes with viscosities of from about 5 to about 100,000 centistokes at 25° C. Among the preferred non-volatile emollients useful in the present compositions are the polydimethyl siloxanes having viscosities from about 10 to about 400 centistokes at 25° C. Such polyalkyl siloxanes include the Vicasil series (sold by General Electric Company) and the Dow Corning 200 series (sold by Dow Corning Corporation). Polyalkylaryl siloxanes include polymethylphenyl siloxanes having viscosities of from about 15 to about 65 centistokes at 25° C. These are available, for example, as SF 1075 methylphenyl fluid (sold by General Electric Company) and 556 Cosmetic Grade Fluid (sold by Dow Corning Corporation). Useful polyether siloxane copolymers include, for example, a polyoxyalkylene ether copolymer having a viscosity of about 1200 to 1500 centistokes at 25° C. Such a fluid is available as SF-1066 organosilicone surfactant (sold by General Electric Company). Polysiloxane ethylene glycol ether copolymers are preferred copolymers for use in the present compositions.

Non-polar fatty acid and fatty alcohol esters useful herein as an emollient material include, for example, di-isopropyl adipate, isopropyl myristate, isopropyl palmitate, ethyl hexyl palmitate, isodecyl neopentanoate $C_{12}$-$C_{15}$ alcohol benzoate, isodecyl oleate, diethyl hexyl maleate, PPG-14 butyl ether and PPG-2 myristyl ether propionate. Petrolatum and USP light (e.g. Klearol ®) or heavy (e.g. Kaydol ®) mineral oils are also useful as emollients.

The emollients typically comprise in total from about 2% to about 10%, and most preferably from about 2% to about 6% by weight of the compositions of the present invention.

Particularly preferred for use in the cleansing compositions of the present invention is a highly branched hydrocarbon compound of the formula:

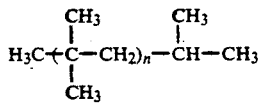

wherein n is an integer from 1 to 225, preferably from 1 to 214 more preferably from 1 to 16, more preferably 1 to 4, and most preferably from 2 to 4. These highly branched hydrocarbon compounds have a molecular weight ranging from about 170 to about 12,000 and are available from Presperse Inc. (South Plainfield, N.J.) as the Permethyl ® 99A-108A Series. These permethyl compounds are present at a level of from about 1% to about 30%, preferably from about 1% to about 10% and most preferably from about 1% to about 5%.

The cleaning compositions of the present invention can optionally contain, at their art-established levels, other materials which are conventionally used in skin cleansing compositions.

Various water-soluble materials may also be present in the compositions of this invention. These include humectants, such as glycerin, sorbitol, hexylene glycol, propylene glycol, polyethylene glycol, alkoxylated glucose and hexanetriol, ethyl cellulose, polyvinyl alcohol, carboxymethyl cellulose, vegetable gums and clays such as Veegum ® (magnesium aluminum silicate, R.T. Vanderbilt, Inc.); proteins and polypeptides; preservatives such as the methyl, ethyl, propyl and butyl esters of hydroxybenzoic acid (Parabens—Mallinckrodt Chemical Corporation), EDTA, methylisothiazolinone and imidazolidinyl ureas (Germall ® 115—Sutton Laboratories); and alkaline agent such as triethanolamine to neutralize, if desired, part of the fatty acids or thickener which may be present. In addition, the topical compositions herein can contain conventional cosmetic adjuvants, such as dyes, opacifiers (e.g., titanium dioxide), pigments and perfumes.

Various vitamins may also be included in the compositions of the present invention. For example, Vitamin A, and derivatives thereof, Vitamin B, biotin, pantothenic, Vitamin D, and mixtures thereof may be used. Vitamin E, tocopherol acetate and derivatives may also be used.

Conventional antibacterial agents and sanitizers can be included in the skin cleansing compositions at levels of from about 0.5% to about 4%. Typical antibacterial sanitizers which are suitable for use herein include 3,4-di- and 3,4',5'-tri-bromo-salicylanilides; 4,4'-dichloro-3-(trifluoromethyl) carbanilide; 3,4,4'-trichlorocarbanilide and mixtures of these materials. Use of these and related materials in skin cleansing compositions is described in more detail in Reller, et al., U.S. Pat. No. 3,256,200, issued June 14, 1966, incorporated herein by reference.

Free fatty acid, such as coconut oil fatty acid, can be added to the compositions herein at levels up to about 10% to improve the volume and quality (creaminess) of the lather produced by the compositions.

The topical compositions of the present invention may contain, in addition to the aforementioned components, a wide variety of additional oil-soluble materials and/or water-soluble materials conventionally used in topical compositions, at their art-established levels.

A particularly preferred optional ingredient is a cationic or nonionic polymeric skin feel aid. Reduced skin irritation benefits of both types of polymers are set out in "Polymer JR for Skin Care" Bulletin, by Union Carbide, 1977. The cationics are preferred over the nonionics, for use herein, because they provide better skin feel benefits. Examples of the cationic polymers and the nonionic polymers useful for this purpose are set out below.

The amount of polymeric skin feel aid found useful in the present invention is from about 0.5% to about 5%, preferably from about 0.1% to about 2%, and more preferably from about 0.1% to about 1%, of the composition.

A particularly preferred skin feel aid is cationic (quaternized) guar gum, e.g., Jaguar C-14-S, from Celanese Corporation.

Other types of high molecular weight polymeric skin feel agents useful herein include nonionic guar gums, Merquats 100 and 550, made by Merck & Co., Inc.; UCARE ® polymer JR-400, made by Union Carbide Corp. Mirapol ® A15 made by Miranol Chemical Company, Inc.; and Galactasol ® 811, made by Henkel, Inc.

The nonionic polymers found to be useful as skin feel aids include the nonionic polysaccharides, e.g., nonionic hydroxypropyl guar gums, sold by Celanese Water Soluble Polymers, a Division of Celanese Corp. A preferred nonionic hydroxypropyl guar gum material is Jaguar ® HP-60 having hydroxypropyl molar substitution of about 0.6. Another class of useful nonionic skin feel aids include cellulose nonionic polymers, e.g., hydroxyethylcellulose and carboxymethylcellulose.

The physical form of the skin cleansing compositions is not critical. The compositions can be, for example, formulated as creams, lotions and the like using art-recognized techniques.

The following non-limiting examples illustrate embodiments of the subject invention wherein both essential and optional ingredients are combined. It is to be understood that these examples are for illustrative purposes only and are not to be construed as limiting the scope of the invention thereto.

EXAMPLE I

A facial cleansing composition of the present invention is made as follows:

| Ingredient | % W/W |
| --- | --- |
| Phase A | |
| Water | q.s |
| Carbomer 1342 | 0.20 |
| Glycerin | 6.00 |
| Hexylene glycol | 2.00 |
| Phase B | |
| Mineral Oil | 13.00 |
| Polyalphaolfin 2 cst.[1] | 9.00 |
| Isododecane[2] | 5.00 |
| Polyethylene glycol-8 Laurate[3] | 1.60 |
| $C_{12}$-$C_{16}$ Glycoside[4] | 3.50 |
| Sorbitan stearate[5] | 2.15 |
| Stearyl Alcohol | 1.60 |
| Ceteareth-20 | 1.00 |
| Cetyl Alcohol | 0.70 |
| Phase C | |
| Water | 1.00 |
| Triethanolamine | 0.20 |
| Phase D | |
| Water | 1.00 |
| Methylchloroisothiazolonone (and) Methylisothiazolinone[6] | 0.06 |

[1] Available As Emerest ® 3002 from Quantum-Emery Division
[2] Available as Permethyl ® 99A from Presperse Inc.
[3] Available as Pegosperse ® 400 ML from Lonza Inc.
[4] Available as APG ® Henkel Corporation
[5] Available as Arlacel ® 60 from ICI Americas
[6] Available as Kathon ® CG from Rohm and Haas Hydrate carbomer Phase A and heat to 70° C. Separately, the components of Phase B are combined and heated to 75° C. Phase B is then added to Phase A while mixing at a moderate rate. Phase C is added to this mixture and the resulting mixture is then cooled to 40° C. Phase D is added to this mixture and this mixture is then cooled to 30° C.

Application of 2 grams of the resulting emulsion is useful for topical application as a cleanser to remove, for example, dirt and oil as well as difficult to remove make-up, waterproof mascara and the like.

EXAMPLE II

A facial cleansing composition of the present invention is made as follows:

| Ingredient | % W/W |
| --- | --- |
| Phase A | |
| Water | q.s |
| Carbomer 1342 | 0.20 |
| Glycerin | 6.00 |
| Propylene glycol | 2.00 |
| Methylparaben | 0.30 |
| Phase B | |
| Polyalphaolefin 2 cst | 15.00 |
| Mineral Oil | 7.00 |
| Isopropyl Palmitate[1] | 3.00 |
| Dimethicone[2] | 1.00 |
| Steareth-21 | 2.30 |
| Steareth-2 | 2.15 |
| Propylparaben | 0.20 |
| Ethylparaben | 0.20 |
| Phase C | |
| Water | 1.00 |
| Triethanloamine | 0.20 |
| Phase D | |
| Water | 1.00 |
| DMDM Hydantoin[3] | 0.50 |
| Mixed Ether Sulfates[4] | 3.50 |

[1] Available as Wickenol ® from Wicken Chemicals
[2] Available as Dow Corning 225 Fluid from Dow Corning
[3] Available as Glydrant ® from Glyco
[4] Available as Texapon ® ASV from Henkel Corporation Hydrate carbomer Phase A and heat to 70° C. Separately, the components of Phase B are combined and heated to 75° C. Phase B is then added to Phase A while mixing at a moderate rate. Phase C is added to this mixture and the resulting mixture is then cooled to 40° C. Phase D and Phase E are added to this mixture and this mixture is then cooled to 30° C.

Application of 2 grams of the resulting emulsion is useful for topical application as a cleanser to remove, for example, dirt and oil as well as difficult to remove make-up, waterproof mascara and the like.

EXAMPLE III

A facial cleansing composition of the present invention is made as follows:

| Ingredient | % W/W |
| --- | --- |
| Phase A | |
| Water | q.s |
| Carbomer 1342 | 0.15 |
| Glycerin | 5.50 |
| Propylene glycol | 1.50 |
| Methylparaben | 0.30 |
| Phase B | |
| Polyalphaolefin 2 cst | 14.00 |
| Isopropyl palmitate | 8.00 |
| Isodecyl oleate | 4.00 |
| Dimethicone | 1.00 |
| Polyethylene Glycol-8 Laurate | 3.25 |
| Glyceryl Monostearate SE[1] | 3.00 |
| Stearyl Alcohol | 1.80 |
| Cetyl Alcohol | 1.80 |
| Ceteareth-20 | 1.20 |
| Propylparaben | 0.20 |
| Ethylparaben | 0.20 |
| Phase C | |
| Water | 1.00 |
| Triethanolamine | 0.15 |
| Phase D | |
| Water | 1.00 |
| Imidazolidinyl Urea | 0.50 |
| Phase E | |
| Fragrance | 0.25 |

[1] Available as Cerasynt ® WM from Van Dyke

Hydrate carbomer Phase A and heat to 70° C. Separately, the components of Phase B are combined and heated to 75° C. Phase B is then added to Phase A while mixing at a moderate rate. Phase C is added to this mixture and the resulting mixture is then cooled to 40° C. Phase D and Phase E are added to this mixture and this mixture is then cooled to 30° C.

Application of 2 grams of the resulting emulsion is useful for topical application as a cleanser to remove, for example, dirt and oil as well as difficult to remove make-up, waterproof mascara and the like.

EXAMPLE IV

A facial cleansing composition of the present invention is made as follows:

| Ingredient | % W/W |
| --- | --- |
| Phase A | |
| Water | q.s |
| Carbomer 1342 | 0.30 |
| Glycerin | 5.50 |
| Propylene glycol | 2.00 |
| Methylparaben | 0.30 |
| Mixed Ether Sulfates | 2.50 |
| Phase B | |
| Polyalphaolefin 2 cst | 11.50 |
| Dioctyl Maleate[1] | 9.00 |
| Isohexadecane[2] | 4.75 |
| Cyclomethicone[3] | 1.00 |
| Caprylyl/Capryl glucoside[4] | 3.25 |
| Stearyl Alcohol | 2.00 |
| Cetyl Alcohol | 1.80 |
| Ceteareth-20 | 1.50 |
| Propylparaben | 0.20 |
| Ethylparaben | 0.20 |
| Phase C | |
| Water | 1.00 |
| Triethanolamine | 0.30 |
| Phase D | |
| Water | 1.00 |
| Imidazolidinyl urea | 0.50 |
| FD&C Blue #1 (0.10% solution) | 0.10 |
| Phase E | |
| Fragrance | 0.15 |

[1] Available as Bernel ® Ester DOM from Bernel
[2] Available as Permethyl ® from Presperse Inc.
[3] Available as Dow Corning 345 from Dow Corning
[4] Available as Triton ® CG 110 from Rohm and Haas Hydrate carbomer Phase A and heat to 70° C. Separately, the components of Phase B are combined and heated to 75° C. Phase B is then added to Phase A while mixing at a moderate rate. Phase C is added to this mixture and the resulting mixture is then cooled to 40° C. Phase D and Phase E are added to this mixture and this mixture is then cooled to 30° C.

Application of 2 grams of the resulting emulsion is useful for topical application as a cleanser to remove, for example, dirt and oil as well as difficult to remove make-up, waterproof mascara and the like.

What is claimed is:

1. A cleansing composition for removing make-up in the form of an oil-in-water emulsion comprising:
   a. from about 0.5% to about 10% of a surfactant with an HLB greater than about 10 selected from the group consisting of anionic, nonionic, zwitterionic, amphoteric and ampholytic surfactants and mixtures thereof;
   b. from about 2% to 30% of polyalphaolefin of the formula:
   $$R_1\text{—}C\text{=}C\text{—}R_2$$
   wherein $R_1$ and $R_2$ are independently from about $C_{20}$ to about $C_{30}$ alkyl, wherein said polyalphaolefin has a viscosity of from about 2 to about 4 centistokes at 100° C.; and
   c. from about 0.025% to about 0.75% of a carboxylic copolymer comprising polymers of a monomeric mixture containing 95.9 to 98.8 weight percent of an olefinically unsaturated carboxylic monomer selected from the group consisting of acrylic, methacrylic and ethacrylic acids, about 1 to about 3.5 weight percent of an acrylate ester of the formula:

$$CH_2\text{=}\underset{\underset{R_1}{|}}{C}\text{—}\overset{\overset{O}{\|}}{C}\text{—}O\text{—}R$$

wherein R is an alkyl radical containing 10 to 30 carbon atoms and $R_1$ is hydrogen, methyl or ethyl, and 0.1 to 0.6 weight percent of a polymerizable cross-linking polyalkenyl polyether of a polyhydric alcohol containing more than one alkenyl ether group per molecule wherein the parent polyhydric alcohol contains at least 3 carbon atoms and at least 3 hydroxyl groups.

2. A cleansing composition according to claim 1 which comprises from about 0.5% to about 5% of said surfactant and wherein said surfactant is selected from the group consisting of anionic surfactants, nonionic surfactants and mixtures thereof and which comprises from about 5% to about 15% of the polyalphaolefin.

3. A cleansing composition according to claim 2 which further comprises from about 1% to about 30% of a highly branched hydrocarbon of the formula:

$$H_3C\text{—}\underset{\underset{CH_3}{|}}{\overset{\overset{CH_3}{|}}{C}}\text{(—}CH_2\text{)}_n\text{—}\underset{}{\overset{\overset{CH_3}{|}}{CH}}\text{—}CH_3$$

wherein n is an integer from 1 to 225.

4. A cleansing composition according to claim 3 which comprises from about 1% to about 10% of said highly branched hydrocarbon and wherein n is an integer from 1 to 16.

5. A cleansing composition according to claim 4 which comprises from about 0.5% to about 2% of said surfactant and from about 1% to about 5% of the highly branched hydrocarbon component and wherein n is an integer from 1 to 4.

6. A cleansing composition according to claim 5 which comprises from about 8% to about 11% of said polyalphaolefin.

7. A cleansing composition according to claim 6 which further comprises from about 0.05% to about 10% of an emulsifier.

8. A cleansing composition according to claim 7 which comprises from about 2% to about 8% of said emulsifier.

9. A cleansing composition according to claim 8 which further comprises from about 2% to about 10% of an emollient.

10. A cleansing composition according to claim 9 wherein said emollient is selected from the group consisting of volatile silicone oils and non-volatile emollients and mixtures thereof.

* * * * *